United States Patent
Souzy et al.

(10) Patent No.: US 8,957,008 B2
(45) Date of Patent: Feb. 17, 2015

(54) AGENT FOR OBTAINING A STABLE AQUEOUS COMPOSITION COMPRISING PARTICLES IN SUSPENSION

(71) Applicant: Coatex, Genay (FR)

(72) Inventors: Renaud Souzy, Caluire et Cuire (FR); Yves Kensicher, Theize (FR); Olivier Guerret, Pern (FR)

(73) Assignee: Coatex, Genay (FR)

( * ) Notice: Subject to any disclaimer, the term of this patent is extended or adjusted under 35 U.S.C. 154(b) by 0 days.

(21) Appl. No.: 14/133,735

(22) Filed: Dec. 19, 2013

(65) Prior Publication Data

US 2014/0179580 A1 Jun. 26, 2014

Related U.S. Application Data

(60) Provisional application No. 61/740,487, filed on Dec. 21, 2012.

(30) Foreign Application Priority Data

Dec. 20, 2012 (FR) .................................... 12 62416

(51) Int. Cl.
| | |
|---|---|
| *C11D 1/72* | (2006.01) |
| *A61Q 5/02* | (2006.01) |
| *A61K 8/81* | (2006.01) |
| *C08K 5/06* | (2006.01) |
| *C08L 33/08* | (2006.01) |
| *A61K 8/84* | (2006.01) |
| *A61K 8/04* | (2006.01) |
| *A61K 8/86* | (2006.01) |
| *A61K 8/02* | (2006.01) |

(52) U.S. Cl.
CPC . *A61K 8/84* (2013.01); *A61K 8/044* (2013.01); *A61Q 5/02* (2013.01); *C08K 5/06* (2013.01); *C08L 33/08* (2013.01); *A61K 8/86* (2013.01); *A61K 8/8152* (2013.01); *A61K 8/0241* (2013.01); *A61K 2800/48* (2013.01)
USPC ........... 510/421; 510/418; 510/434; 510/437; 510/475; 510/477; 424/401; 424/487; 424/70.16; 424/70.31

(58) Field of Classification Search
USPC ................. 510/418, 421, 434, 437, 475, 477; 424/401, 487, 70.16, 70.31
See application file for complete search history.

(56) References Cited

U.S. PATENT DOCUMENTS 4,954,283 A * 9/1990 Schmid et al. ................ 510/467
2005/0175568 A1 8/2005 Asari et al.

FOREIGN PATENT DOCUMENTS

DE 10 2004 029 328 A1 12/2005

OTHER PUBLICATIONS

International Search Report issued Mar. 12, 2014 in PCT/FR2013/053176 (with English translation of categories of cited documents).

* cited by examiner

*Primary Examiner* — Brian P Mruk
(74) *Attorney, Agent, or Firm* — Oblon, Spivak, McClelland, Maier & Neustadt, L.L.P.

(57) ABSTRACT

Agent for obtaining a stable aqueous composition comprising an association:
of a polymer constituted by:
at least one A monomer of acrylic acid and/or methacrylic acid and/or any of their salts,
at least one B monomer of alkyl acrylate and/or methacrylate, and
At least one crosslinking D monomer, and
with at least one C compound corresponding to the following formulae (I):

$$R1\text{-}O\text{-}[(EO)_n(PO)_{n'}(BO)_{n''}]\text{-}Z \qquad (I)$$

in which:
R1 represents an ethyl, isopropyl or sec-butyl radical,
$[(EO)_n(PO)_{n'}(BO)_{n''}]$ represents a polyalkoxylated chain constituted of alkoxylated units, distributed into blocks, alternatively or statistically, chosen from among EO ethoxylated units, PO propoxylated units and BO butoxylated units, representing, independently from each other, 0 or a whole number between 1 and 150, the sum of n, n' and n'' not being null, and
Z represents a fatty chain, linear or branched, of at least 16 carbon atoms.

12 Claims, No Drawings

AGENT FOR OBTAINING A STABLE AQUEOUS COMPOSITION COMPRISING PARTICLES IN SUSPENSION

REFERENCE TO PRIOR APPLICATIONS

This application claims priority to U.S. provisional application Ser. No. 61/740,487, filed Dec. 21, 2012; and to French patent application 12 62416, filed Dec. 20, 2012, both incorporated herein by reference.

This invention concerns the formulation of stable aqueous compositions comprising particles in suspension.

The problem encountered in formulating these compositions mainly lies in a homogenous distribution of particles in the composition and their stability over time, particularly during storage. In the preparation of these compositions, this parameter is of course merely one criterion to be met among other essential ones, such as viscosity, pH, clarity, stability . . . . It is therefore necessary to achieve an optimum adjustment of all of these parameters, and this is an objective of the invention.

In the following description, reference is made to the formulation of cosmetic compositions, but the invention is not restricted to this scope of application, and extends to any other sector implementing such compositions, such as detergents.

In his article for Cosmetics & Toiletries® review, vol. 123, N. 12 of December 2008, "Formulating at pH 4-5: How Lower pH Benefits the Skin and Formulations", J W Wiechers expresses his surprise that, the skin's natural pH being acid, at around 4.7, most available cosmetic compositions have a higher pH, of around 6 and above. Such pH variations are not without impact on a skin that is regularly subject to them, for example in terms of the development of human cutaneous micro flora, and he highlights the benefits conferred by cosmetic formulations with a pH close to 4.7. In particular he observes increased penetration of certain active principles, as well as better preservation of same at these pH values, making it possible to limit the use of preservatives.

In addition to the problem raised by the presence of particles, a formulator of acid aqueous compositions encounters difficulties, because the continuous phase of these compositions is not stable, rapidly evolving towards a dephasing. This phenomenon is particularly visible when compositions comprise particles in suspension, which can also be dragged to the bottom or surface of the container.

The document WO 03/061615A describes cosmetic compositions formulated at a pH of between 6 and 7, used as a hair fixing agent. They contain a thickener consisting of a HASE (hydrophobically modified alkali-swellable) polymer, obtained through the polymerisation of methacrylic acid, of ethyl acrylate, of hydrophobic monomer comprising a polymiserable end such as acrylic acid, an ethoxylated mid part and a hydrophobic end consisting of a linear hydrocarbonated fatty chain and a crosslinking monomer. The compositions thus formulated have a rheology such, that they are sprayable, and do not flow on the hair, while drying rapidly once applied. This document mainly describes the properties of compounds, when used.

The problem that the invention seeks to resolve is the preparation of aqueous compositions, comprising a continuous limpid phase and particles in suspension distributed in the continuous phase, the pH of these compositions being less than 7, and these compositions being stable. An important effect is that, particularly during storage of such compositions, particles are kept in suspension in the continuous phase, which remains limpid. It must be possible to visualise these particles, having a technical or merely aesthetic function, and they must therefore be visible, at any moment.

Curiously, authors have observed that there is no correlation between the viscosity of a composition given by a thickener and the capacity of the latter to keep particles in suspension in the composition.

According to the invention, an association of a polymer and a fatty chain has been discovered for the formulation of aqueous acid compositions, in which this association acts as both a thickener and clarifier in the continuous phase, while allowing an even distribution of particles in the continuous phase, said compositions remaining stable over time, and in particular visibly stable.

The invention's association consists:
of a polymer which is obtained from the following monomers:
At least one A monomer of acrylic acid and/or methacrylic acid and/or any of their salts,
At least one B monomer of alkyl acrylate and/or methacrylate, and
At least one crosslinking D monomer, and
At least one C fatty chain corresponding to the following formulae (I):

$$R1O\text{-}[(EO)_n(PO)_{n'}(BO)_{n''}]\text{—}Z \qquad (I)$$

in which:
R1 represents an ethyl, isopropyl or sec-butyl radical,
$[(EO)_n(PO)_{n'}(BO)_{n''}]$ represents a polyalkoxylated chain consisting of alkoxylated units, distributed into blocks, alternatively or statistically, chosen from among EO ethoxylated units, PO propoxylated units and BO butoxylated units,
n, n', n" representing, independently of each other, 0 or a whole number varying from 1 to 150, the sum of n, n' and n" not being null, and
Z representing a fatty chain, linear or branched, of at least 16 carbon atoms.

Thus, the invention concerns an agent for the obtention of a stable aqueous composition, comprising a limpid phase and particles in suspension distributed in the continuous phase, and having a pH of less than 7, comprising an association of a polymer resulting from the polymerisation of the A, B and D monomers above, and the C compound above. It also concerns the aqueous and stable composition, thus prepared.

Before discussing the invention and its applications in more detail, certain terms used in the description and the claims are defined below.

A composition of the invention may comprise at least one active ingredient (or active agent) or a mixture of active ingredients, in any form whatsoever, and whatever the field of application of the composition, as indicated above.

The active principle/s may be dissolved in the continuous phase of the composition, and/or in particulate form, non-soluble in the continuous phase, and constitute all or part of the particles in suspension.

By "particles to be in suspension to obtain a composition of the invention", we mean solid bodies, these bodies being plain or hollow, liquid or gassy, and being possibly characterised by different forms, textures, structures, compositions, colours and final properties. By way of example we can mention exfoliating particles (for example polyethylene particles, crushed fruit shells, pumice stones), nourishing particles (for example collagen spheres), pearlescent particles (for example titanium mica, distearate glycols) and aesthetic particles (for example air bubbles, flakes, pigments, possibly coloured). In respect of the suspension of air bubbles in the composition, particles can be of a size of the order of 1, 2 or 3 mm per example.

By "Alkyl" we mean a $C_mH_{2m+1}$ group, linear or branched, where m varies from 1 to 10, or from 1 to 6, or from 1 to 3, or 1 to 2. According to some embodiments, having regard to the monomers available on the market, this is a methyl or ethyl group.

By "PO propoxylated units" and "BO butoxylated units", we mean ethoxylated units carrying, on one or other of their carbons, respectively a methyl or ethyl radical. An ethoxylated unit is a —$CH_2$—$CH_2$—O unit.

By "fatty chain" we mean an aliphatic hydrocarbonated chain of a fatty acid, linear or branched, comprising at least 16 carbon atoms, or 16 to 36 carbon atoms, or 16 to 32 carbon atoms.

According to the invention, the clarity or limpidity of a composition is measured by its transmittance. A method for determining the transmittance is described below in example 1, Materials and methods. It is expressed in a percentage, and a composition is considered as clear or limpid if it presents a transmittance of at least 40%.

In addition to the clarity it adds, the invention agent makes it possible to keep any particle present in the composition in suspension. The use of a composition thus formulated therefore does not require any mixing stage, even if the composition has been stored for several weeks, indeed several months.

The invention agent is particularly well suited to the preparation of a composition having a pH less than or equal to 5.5, or between 4 and 5. Such pH are close to the average pH value of the human skin, and it is thus of major interest in cosmetics.

The agent thus defined preferably has the following characteristics, considered alone or in combination:

The agent according to the present invention includes one or more cross-linking monomers D). According to one embodiment, it has a single cross-linking monomer. According to another embodiment, it has two cross-linking monomers. The cross-linking monomer(s) is (are) used to prepare a copolymer in the form of a three-dimensional network.

According to the present invention, the monomer that is used is a polyunsaturated compound. This compound can have two, three or more ethylenic unsaturations.

The cross-linking monomer can have a hydrophilic, hydrophobic or amphiphilic character.

Examples of these compounds include the di(meth)acrylate compounds such as di(meth)acrylate of ethylene glycol, di(meth)acrylate of polyethylene glycol, di(meth)acrylate of triethylene glycol, di(meth)acrylate of 1,3-butylene glycol, 1,6-butylene glycol di(meth)acrylate, 1,6-hexanediol di(meth)acrylate, neopentyl glycol di(meth)acrylate, 1,9-nonanediol di(meth)acrylate, 2,2'-bis(4-(acryloxy-propyloxyphenyl)propane, 2,2'-bis(4-(acryloxydiethoxy-phenyl)propane, and zinc acrylate; the tri(meth)acrylate compounds such as tri(meth)acrylate of trimethylolpropane, tri(meth)acrylate trimethyloletrane, tri(meth)acrylate pentaerythritol and tri(meth)acrylate of tetramethylolmethane; the tetra(meth)acrylate compounds such as ditrimethylolpropane tetra(meth)acrylate, tetramethylolmethane tetra(meth)acrylate, and pentaerythritol tetra(meth)acrylate; the hexa(meth)acrylate compounds such as dipentaerythritol hexa(meth)acrylate; the penta(meth)acrylate compounds such as the penta(meth)acrylate of dipentaerythritol; the allyl compounds such as allyl (meth)acrylate, diallylphthalate, diallyl itaconate, diallyl fumarate, and diallyl maleate; the polyallyl ethers of sucrose with from 2 to 8 groups per molecule, the polyallyl ethers of pentaerythritol such as pentaerythritol diallyl ether, pentaerythritol triallyl ether, and pentaerythritol tetraallyl ether; the polyallyl ethers of trimethylolpropane such as trimethylolpropane diallyl ether and trimethylolpropane triallyl ether. Other polyunsaturated compounds include divinyl glycol, divinyl benzene, divinylcyclohexyl and methylenebisacrylamide.

According to another aspect, the cross-linking monomers can be prepared by a reaction of esterification of a polyol with an unsaturated anhydride such as maleic anhydride or itaconic anhydride, or by a reaction of addition with an isocyanate such as 3-isopropenyl-dimethylbenzene isocyanate.

The following unsaturated compounds which cross-link by means of their pendant carboxyl groups can also be used: polyhaloalkanols such as 1,3-dichloroisopropanol and 1,3-dibromoisopropanol; haloepoxyalkanes such as epichlorohydrin, epibromohydrin, 2-methyl epichlorohydrin, and epiiodohydrin; polyglycidyl ethers such as 1,4-butanediol diglycidyl ether, glycerine-1,3-diglycidyl ether, ethylene glycol diglycidyl ether, propylene glycol diglycidyl ether, diethylene glycol diglycidyl ether, neopentyl glycol diglycidyl ether, polypropylene glycol diglycidyl ethers, bisphenol A-epichlorohydrin epoxy resins and mixtures.

The proportion of A, B and D monomers may vary from 11-52%, from 41-82% and from 0.05-12%, respectively, by weight compared with the total weight of the polymer.

According to one embodiment, it varies from 31-47%, from 51-67%, and from 0.5-5%, respectively, by weight compared with the total weight of the polymer.

Put another way, the proportion of A, B and D monomers varies from 10-50%, from 40-80% and from 0.05-10%, respectively or from 30-40%, from 50-65% and from 0.5-5% by weight compared with the total weight of the polymer/C compound association.

In the association of the invention, the proportion of the polymer varies from 80-99.9%, or from 90-99.5%, and that of the C composition varies from 0.1-20%, or from 0.5-10%, compared with the total weight of the association.

Polymers are prepared according to procedures known to the person skilled in the art. More precisely, they are obtained by procedures known as conventional radical co-polymerization in solution, in direct or inverse emulsion in bulk, in suspension or precipitation in the appropriate solvents, in the presence of known initiators and transfer agents, or by controlled radical polymerization procedures, such as the method called Reversible Addition Fragmentation Transfer (RAFT), the method called Atom Transfer Radical Polymerization (ATRP), the method called Nitroxide Mediated Polymerization (NMP), or the method called Cobaloxime Mediated Free Radical Polymerization. The polymerization should preferably be realised in emulsion.

The invention also concerns an aqueous cosmetic composition, comprising a continuous phase and particles in suspension in the continuous phase, said continuous phase and/or said particles comprising and/or consisting of an active cosmetic principle, and having a pH lower than 6, or between 4 and 5, said composition comprising an agent as defined above. In respect of active principle/s, they may comprise a cleaning base for the body and/or the hair. In such a composition, the proportion of the invention agent can vary from 0.1 to 20%, or from 5 to 15% by weight compared with the total weight of the composition.

The invention further concerns the use for the preparation of a stable aqueous composition, comprising a continuous limpid phase and particles in suspension distributed in the continuous phase, and having a pH lower than 7, an association of a polymer and a C compound, as defined above.

This invention is now illustrated, non-exhaustively, by the following examples.

Example 1

Materials and Methods

The advantages of the invention can be shown by measuring the properties of the invention compositions, compared with those of compositions comprising a thickening agent known to the person skilled in the art.

Organoleptic Properties of a Composition:

The organoleptic properties of different cosmetic compositions such as shower gel/shampoo, are tested, formulated and stored in a heat chamber (45° C.) for 3 months. The evaluation is carried out at room temperature. The following criteria are taken into account: Opacity (variation from limpid to opaque, indeed intense white), Texture (unctuous, presence of lumps, of grains . . . ), Odour (whether or not there is an odour), Colour (variation in homogeneity), and Surface (smooth or not smooth).

Clarity or Limpidity of a Composition:

Limpidity is measured by measuring transmittance in the following way:

Measurements are taken on a UV Genesys Spectrometer 10 UV™ (Cole Parmer), equipped with Rotilabo-Einmal Kuvetten PS, 4.5 mL vessels. In practical terms, the device is heated 10 minutes before use.

Firstly an initial measurement is carried out using a vessel filled with 3.8 ml of bipermuted water (the "blank").

The measurement is then taken with a vessel filled with 3.8 mL of the solution of cosmetic composition to be tested. The transmittance is then measured with a wave length of 500 nm. The higher the transmittance value, expressed in %, the more limpid the cosmetic composition is.

As stated above, the composition is considered to be limpid at a transmittance value of at least 40%.

Visco-Elasticity of a Composition:

Visco-elasticity measurements of different formulations are carried out with the help of a Haake-RheoStress RS 150 type rheometer. The variation of the angle of dephasing ($\delta$, in)°, depending on the constraint $\tau$ (scanning from 0 to 800 Pa) is measured at 25° C., thanks to the cone-plate modulus (1°). The flow limit value (YV, Pa or Dyn/cm$^2$) is deduced from these measurements.

Stability of a Composition:

A stability test of different sun protection formulae is carried out:

at t=1 month—Sample stored at +4° C.

at t=3 months—Sample stored at +45° C.

Potential instabilities such as the dephasing, creaming, bleeding, release, deposit/sedimentation are observed.

Viscosity of a Composition:

The viscosity of said formulations is measured using a Brookfield viscometer, RVT model. Before measuring viscosity, each formulation is left to rest 24 hours at 25° C. The spindle must be centred on the flask's opening. Then, viscosity is measured at 6 rpm (rotations per minute) using the appropriate modulus. The viscometer is left to rotate until the viscosity is stable.

Example 2

Ultra-Soft Exfoliating Shampoo

This example illustrates the use of an agent according to the invention in ultra-soft shampoo type cosmetic formulation, and aims to show the rheological (suspension and viscosity) and organoleptic properties provided by this agent.

Thus, from a shampoo formulation based on anionic and zwitterionic surfactants, the composition of which is shown in table 1, the aim is to verify in this formula the limpidity, viscosity and suspension as affected by different rheology modifiers, including those of prior art and those according to the invention. The values mentioned in the last column of the table indicate the in grams.

TABLE 1

| | |
|---|---|
| 1 - DI water | QSF 100 |
| 2-Texapon NSO UP, 28 (Cognis) | 32.14 |
| 3-Dehyton PK 45 (Cognis) | 6.67 |
| 4 --Rheology Modifier | Qs 10000 ± 500 cPs |
| 5- Sodium Hydroxide | Qs pH = 6.0 or 7.0 ± 0.1 |
| 6-Lactic Acid | Qs pH 5.0 ± 0.1 |
| 7-Potassium sorbate (Nutrinova) | 0.40 |
| 8-Strawberry Fragrance (Hyteck) | 0.50 |
| 9-Exfoson Quin 300 red, Exfoliating particles (Soniam) | 2.00 |

Formulation Preparation Protocol:

The bipermuted water (1) is placed in a beaker, and then the different ingredients (2) and (3) are added under stirring.

After total homogenization, the rheology modifier (4) is very gently added under stirring.

The pH is measured, which is then adjusted to 5.0±0.1 or 6.0±0.1 or 7.0±0.1 with the ingredients (5) or (6).

After verifying the pH, the preserver (7) and the perfume (8) are mixed, with moderate stirring, into the shampoo formulation.

The exfoliating quinoa particles (9) are then dispersed, under stirring.

Table 2 summarises all the rheology modifiers that have been used as an ingredient (4) within the framework of tests of this example 1. Note that their quantity is expressed by weight percentage compared with the total weight of the composition. By way of example, if it is equal to 5%, we add 5 g of (4) for a formulation of 100 g of finished product.

The application results are presented in Tables 2 and 3.

TABLE 2

| Test | Physical solid State at 100% of active matter | Physical state Aqueous solution % of Active Matter | Z (%) | Rheological Additive Composition (weight %) | | | | Z | n' | n | Ramification Z |
|---|---|---|---|---|---|---|---|---|---|---|---|
| | | | | Acrylic Ester B | Methacrylic Acid A | Difunctional Monomer D | Macro-Surfactant C | | | | |
| 1-1 (REF) | Yes | NA | 3.0 | NA | NA | NA | NA | NA | NA | NA | NA |
| 1-2 (PA) | Yes | NA | 3.0 | NA | NA | NA | NA | NA | NA | NA | NA |
| 1-3 (PA) | NA | 30.0 | 10.0 | 53.5 | 43.1 | 3.4 | 0 | NA | NA | NA | NA |

TABLE 2-continued

| Test | Physical solid State at 100% of active matter | Physical state Aqueous solution % of Active Matter | Z (%) | Rheological Additive Composition (weight %) | | | | Z | n' | n | Ramification Z |
|---|---|---|---|---|---|---|---|---|---|---|---|
| | | | | Acrylic Ester B | Methacrylic Acid A | Difunctional Monomer D | Macro-Surfactant C | | | | |
| 1-4 (INV) | NA | 30.0 | 10.0 | 58.1 | 36.6 | 4.4 | 0.9 | 16 | 0 | 25 | Yes |
| 1-5 (OI) | NA | 30.0 | 10.0 | 52.6 | 37.1 | 5.1 | 5.2 | 12 | 0 | 23 | No |

REF: Reference/PA: Prior Art/INV: Invention/OI: Outside Invention/CONT: Control/NA: Not applicable
Test 1-1: The ingredient (4) here is an inorganic salt: Sodium chloride
Test 1-2: The ingredient (4) here is a crosslinked polymer additive, of the crosslinked polyacrylate type, Carbopol ® ETD (Lubrizol)
Test 1-3: The ingredient (4) here is an ethyl acid/methacrylic acid crosslinked ASE polymer additive
Test 1-5: The ingredient (4) here is a polymer resulting from the polymerisation of monomers A, B, D and monomer C according to the formula T-[(EO)$_n$(PO)$_{n'}$(BO)$_{n''}$]-Z, in which T represents a methacrylate enabling the co-polymerisation of monomer C.

TABLE 3

| | pH 5 | | | | pH 6 | | | | pH 7 | | | |
|---|---|---|---|---|---|---|---|---|---|---|---|---|
| Test | Brookfield Viscosity 6 rpm (cPs) $T_{24}$ | Transmittance (500 nm) | Delta | YV (dyn/cm$^2$) | Brookfield Viscosity 6 rpm (cPs) $T_{24}$ | Transmittance (500 nm) | Delta | YV (dyn/cm$^2$) | Brookfield Viscosity 6 rpm (cPs) $T_{24}$ | Transmittance (500 nm) | Delta | YV (dyn/cm$^2$) |
| 1-1 | 26900 | 98.4% | 43.4° | 0 | 25200 | 98.4% | 42.4° | 0 | 17800 | 98.6% | 48.6° | 0 |
| 1-2 | 6880 | 0.5% | 16.9° | 3 | 9870 | 0.3% | 15.6° | 6 | 11700 | 0.3% | 13.5° | 8 |
| 1-3 | 17640 | 20.4% | 6.9° | 70 | 18420 | 68.2% | 9.3° | 80 | 2075 | 39.7% | 50.3° | 0 |
| 1-4 | 5120 | 42.2% | 10.6° | 15 | 18580 | 75.1% | 9.1° | 60 | 7420 | 91.3% | 22.7° | 20 |
| 1-5 | 7980 | 16.4% | 13.4° | 40 | 9580 | 25.4% | 12.8° | 35 | 15420 | 97.3% | 31.7° | 65 |

The invention claimed is:

1. An agent comprising a polymer and a fatty chain compound of formulae (I), wherein:
   said polymer comprises:
   at least one A monomer selected from acrylic acid, methacrylic acid and their salts,
   at least one B monomer selected from alkyl acrylate and alkyl methacrylate, and
   at least one crosslinking monomer D, and
   formulae (I) is:

$$R_1O-[(EO)_n(PO)_{n'}(BO)_{n''}]—Z \quad (I)$$

in which:
   $R_1$ is an ethyl, isopropyl or sec-butyl radical,
   $[(EO)_n(PO)_{n'}(BO)_{n''}]$ is a polyalkoxylated chain of ethoxylated units EO, propoxylated units PO and butoxylated units BO, distributed into blocks, alternatively or statistically, n, n', n" represent, independently of each other, 0 or a whole number varying from 1 to 150, the sum of n, n' and n" not being zero, and Z is a linear or branched fatty chain of at least 16 carbon atoms.

2. The agent according to claim 1, wherein Z represents a linear or branched fatty chain of 16 to 32 carbon atoms.

3. The agent according to claim 1, wherein said polymer comprises, based on the total weight of the polymer:
   11 to 52% by weight of monomer(s) A,
   41 to 82% by weight of monomer(s) B, and
   0.05% to 12% by weight of monomer(s) D.

4. The agent according to claim 1, wherein said polymer comprises, based on the total weight of the polymer and the fatty chain compound:
   10 to 50% by weight of monomer(s) A,
   40 to 80% by weight of monomer(s) B, and
   0.05% to 10% by weight of monomer(s) D.

5. The agent according to claim 1, comprising 80-99.9% of said polymer and 0.1-20% of said fatty chain compound, based on the total weight of the agent.

6. An aqueous composition comprising water, a continuous phase, particles in suspension in the continuous phase, and the agent according to claim 1.

7. The aqueous composition according to claim 6, wherein the proportion of the agent is 0.1 to 10% by weight compared with the total weight of the composition.

8. The aqueous composition according to claim 6, having a pH less than or equal to 5.5.

9. The aqueous composition according to claim 6, wherein said composition is a cosmetic composition having a pH lower than 7.

10. The aqueous composition according to claim 6, wherein said composition is a cosmetic composition having a pH lower than 6.

11. A method for preparing an aqueous composition having a continuous phase, said method comprising combining water, particles, and the agent according to claim 1 in a manner so as to suspend said particles in the continuous phase of the aqueous composition.

12. A method for suspending particles in a continuous phase of an aqueous composition, said method comprising adding the agent according to claim 1 to said aqueous composition.

* * * * *